United States Patent [19]
Purwar et al.

[11] Patent Number: 5,965,549
[45] Date of Patent: Oct. 12, 1999

[54] CIPROFLOXACIN-HYDROCORTISONE SUSPENSION

[75] Inventors: Shivaji Purwar, Monroe, Conn.; David Goldman, Hillsdale, N.J.

[73] Assignee: Bayer Aktiengesellschaft, Leverkusen, Germany

[21] Appl. No.: 08/801,891

[22] Filed: Feb. 18, 1997

Related U.S. Application Data

[62] Division of application No. 08/465,048, Jun. 6, 1995, abandoned.

[51] Int. Cl.$^6$ .......................... A61K 31/56; A61K 31/495
[52] U.S. Cl. ............................................. 514/177; 514/255
[58] Field of Search ..................................... 514/177, 255

[56] References Cited

U.S. PATENT DOCUMENTS

| | | | |
|---|---|---|---|
| 4,025,620 | 5/1977 | Beyer et al. | 424/115 |
| 4,670,444 | 6/1987 | Grohe | 514/300 |
| 4,844,902 | 7/1989 | Grohe et al. | 424/449 |
| 4,957,922 | 9/1990 | Lammens et al. | 514/255 |
| 5,023,257 | 6/1991 | Pöllinger et al. | 514/254 |
| 5,061,729 | 10/1991 | Kincses et al. | 514/562 |
| 5,260,073 | 11/1993 | Phipps | 424/465 |
| 5,271,939 | 12/1993 | Robertson et al. | 424/427 |
| 5,422,116 | 6/1995 | Yen et al. | 424/427 |

FOREIGN PATENT DOCUMENTS

| | | | |
|---|---|---|---|
| 0689832 | 1/1996 | European Pat. Off. | A61K 9/08 |

OTHER PUBLICATIONS

Strauss, M., et al., Otitis Externa Associated With Aquatic Activities (Swimmer's Ear), Clinics in Dermatology, 1987, pp. 103–111.

Stange, G., et al., Laryngol Rhino Otol 68 (12):653–656 (1989) [Abstract].

Stange, G., et al., Laryngol Rhino Otol 68(12):653–656 (1989).

Esposito, S., et al., Topical and Oral Treatment of Chronic Otitis Media With Ciprofloxacin, Arch Otolaryngol Head Neck Surg—vol. 116, 1990, pp. 557–559.

Garcia–Rodriguez, J.A., et al., Efficacy of 2 Regimens of Local Ciprofloxacin in the Treatment of Ear Infections, Preprint: Drugs 45 (Suppl.), 1993, pp. 40–41.

Ganz, H., Bacterial Otitis Externa Beyond the Organ Limits—Systemic and Topical Combination Treatment with Ciprofloxacin, pp. 2–7 (translation from German).

Garcia–Rodriguez, J.A., Efficacy of Topical Ciprofloxacin in the Treatment of Ear Infections in Adults, J Antimicrob Chemother, 1993, pp. 31:452–453.

Esposito, S., et al., Topical Cirpofloxacin (CP) Versus Parenteral Gentamicin (GM) in Pseudomonas Infections of the Middle Ear, 29. Interscience Conference An Timicrobiotic Agents Chemotherapy +* Houston, 545 (1989) [Abstract].

*Primary Examiner*—Zohreh Fay
*Attorney, Agent, or Firm*—Huw R. Jones; William F. Gray

[57] ABSTRACT

The invention is directed to an aqueous non-ototoxic, topical, otic pharmaceutical composition of matter for treating a mammal consisting essentially of: ciprofloxacin or a pharmaceutically acceptable salt thereof in aqueous solution in an amount effective for antibacterial action; hydrocortisone or a pharmaceutically acceptable salt thereof in an amount effective as an anti-inflammatory agent; polyvinyl alcohol at least about 85% hydrolyzed in an amount effective to suspend the hydrocortisone in solution; water sufficient to produce an aqueous composition; benzyl alcohol in an amount effective for antibacterial action; lecithin in an amount effective for enhancing suspension of other constituents in the composition; and polysorbate ranging from polysorbate 20 to 80 in an amount effective for spreading the preparation on a hydrophobic skin surface to the site of infection or inflammation.

10 Claims, No Drawings

CIPROFLOXACIN-HYDROCORTISONE SUSPENSION

CROSS REFERENCE TO RELATED APPLICATION

This is a divisional application of U.S. Ser. No. 08/465,048 filed Jun. 6, 1995, now abandoned.

FIELD

This invention relates to compositions and methods for treating otitis externa (external ear infections) and otitis media (middle ear infections) specifically otorrhea (otitis media with ruptured ear drum causing effusion).

BACKGROUND

Otitis externa, involving the ear canal portion of the external ear, is a common otologic problem occurring mainly during hot, humid weather, and five times more frequently in swimmers than in nonswimmers. In the incipient stage, symptoms include itching and pain in the ear canal, and tenderness when pressure is applied around the external auditory meatus, the ear lobe is pulled or the jaw is moved. In the definitive stage, suppuration occurs in the ear canal and hearing may be decreased. Over 90% of cases of otitis externa are due to bacterial and fungal infections. Treatment with topical agents is common, including antibacterial and/or antifungal creams and drops. Oral antibiotics may be used if cellulitis symptoms are present.

Otitis media, a term used to describe infections of the middle ear, is also very common. A relatively high percentage of the population, both adults and particularly children, are affected. It has been estimated that nearly 95% of all children experience one or more episodes of otitis by age 9, and that about 15% of all visits by children to pediatricians are in regard to otitis media. In children, the disease is most often associated with upper respiratory afflictions which trigger a transudate secretion response in the Eustachian tube and middle ear. Bacteria and viruses migrate from the naso-pharynx to the middle ear via the Eustachian tube, and can cause the Eustachian tube to become blocked, preventing ventilation and drainage of the middle ear.

In its more severe forms, purulent exudate, toxins and endogenous anti-microbial enzymes are formed in the middle ear, which can cause irreparable damage to sensory-neural and sound conducting structures. It has been reported that sensory-neural hearing loss occurred in 35.8 percent of children with otitis media with effusion. It is estimated that over one billion dollars are spent annually in the United States on the treatment and prevention of otitis media.

Current methods of treatment generally involve the systemic use of antibiotics; the use of ear drops (which have not been approved by the Food and Drug Administration); and in more chronic cases, the insertion of a myringotomy tube through an incision in the eardrum to allow ventilation and drainage of the middle ear cavity. Systemic administration of antibiotics generally requires high initial doses and an appreciable time lag to achieve therapeutic levels in the middle ear. With respect to currently known ear drops, there has been growing concern recently that medications in the middle ear cavity as well as inflammatory and infectious substances can cause inner ear damage. It is generally believed that damaging substances in the middle ear space can gain access into the inner ear across the round window membrane, which has been demonstrated to be semipermeable. Hearing loss is believed a result of impairment, damage or destruction of inner ear cochlear hair cells.

Ciprofloxacin and its preparation is described in U.S. Pat. No. 4,670,444, which is hereby incorporated by reference. Studies have shown the usefulness of local ciprofloxacin in ear infections. A study of the clinical and bacteriological efficacy of ciprofloxacin in human patients affected by chronic otitis media in the acute stage is reported in "Topical and Oral Treatment of Chronic Otitis Media With Ciprofloxacin" by Esposito, D'Errico and Montanaro in *Arch. Otolaryngo Head Neck Surg.*, Vol 116, May 1990, p.556–559. Three drops of ciprofloxacin in saline solution were administered twice a day in affected ears for 5 to 10 days. A high percentage of favorable clinical response and bacteriological eradication was observed without ototoxicity.

A study entitled "Local Therapy for Pseudomonas Infections of the Ear" by G. Stang in *Laryngol Rhino Otol.* 68 (12): 653–656 (1989) reports that infections of the middle and external ear in humans caused by Pseudononas aeruginosa can be cured by local therapy with ciprofloxacin and tutofusin very quickly and without any complications. Function disturbance of the middle and internal ear cleared up and the functions returned to normal.

A study of the "Efficacy of 2 Regimens of Local Ciprofloxacin in the Treatment of Ear Infections" by Garcia-Rodriguez et al was reported in *Preprint: Drugs* 45 (*Suppl.*) 1993, pages 40–41. Ear infections of several types were treated with 3 drops per 8 hours for 7 days with 0.5% ciprofloxacin solution and in another group of patients with 0.3% ciprofloxacin solution. The results obtained showed that local ciprofloxacin is an effective treatment for ear infections with few and mild side effects and without ototoxicity.

While ciprofloxacin-containing ear drops have been prepared and administered in studies, currently, there is no ciprofloxacin or other antibiotic preparation approved for topical middle ear use, and which can be prescribed for a patient. What is needed is a non-irritating, non-sensitizing, non-ototoxic composition which can be readily used by a patient for topical treatment of otitis, particularly otitis media, and most particularly, otorrhea.

SUMMARY

This invention provides a non-ototoxic, non-irritating and non-sensitizing composition for introduction, preferably by instillation, into human and animal ears for the treatment of otitis externa and otitis media, particularly otorrhea. The composition will reach the middle ear through a ruptured ear drum to the site of infection, spread over an infected area, and deposit in a sufficient layer to provide an anti-bacterial effect. The composition comprises ciprofloxacin in an amount effective for antibacterial action; a non-ionic viscosity augmenter unaffected by pH and ionic level in an amount effective for augmenting viscosity of the composition to a viscosity greater than that of water; and water sufficient to produce a liquid composition. The viscosity augmenter is chosen from the group consisting of methylcellulose, polyvinyl alcohol, and glycerine.

One embodiment provides a composition in which all constituents are in solution. The composition comprises: ciprofloxacin in an amount effective for anti-bacterial action; methylcellulose in an amount effective for augmenting the viscosity of the composition to a viscosity greater than that of water; potassium sorbate in an amount effective as a preservative against contamination by microorganisms; sodium acetate and acetic acid in effective amounts for buffering the composition to a pH in a range from about 3 to about 6; a polysorbate ranging from polysorbate 20 to 80 in an effective amount for spreading the composition on a hydrophobic skin surface; and water sufficient to produce a liquid composition.

Another effective composition provided by this embodiment is the latter further comprising glycerin in an effective amount to adjust the tonicity of the composition from about 200 to about 600 milliosmoles, that is, to provide a composition which is approximately isotonic.

Another embodiment provides ciprofloxacin-containing aqueous compositions including an anti-inflammatory agent, preferably hydrocortisone. Hydrocortisone being insoluble in water, the composition is a suspension thereof and comprises: ciprofloxacin in an amount effective for anti-bacterial action; hydrocortisone in an amount effective for anti-inflammatory action; polyvinyl alcohol in an amount effective for augmenting viscosity of the composition to a viscosity greater than that of water and suspending other constituents; lecithin in an amount effective for enhancing suspension of other constituents; benzyl alcohol in an amount effective as a preservative against contamination by microorganisms; sodium acetate and acetic acid in effective amounts for buffering the composition to a pH in the range from about 3 to about 6; a polysorbate ranging from polysorbate 20 to 80 in an effective amount for spreading the composition on a hydrophobic skin surface; and water sufficient to produce a liquid composition.

Another effective suspension composition is the latter further comprising sodium chloride in an effective amount to adjust the tonicity of the composition from about 200 to about 600 milliosmoles, that is,. to render the composition approximately isotonic.

In the compositions including hydrocortisone, each of the other constituents enhance or do not impair the resuspendability of the insoluble constituent hydrocortisone. Therefore a high degree of suspension stability and uniformity is achieved whereby the compositions are stable over long shelf life and are convenient and acceptable to users for topical treatment of conditions such as otitis.

Yet another embodiment provides a composition wherein glycerine augments the viscosity of the aqueous solution to a viscosity greater than that of water. The composition comprises: ciprofloxacin in an amount effective for anti-bacterial action; glycerine in an amount effective for augmenting the viscosity of the composition to a viscosity greater than that of water; and water sufficient to produce a liquid composition.

The invention also provides a method of treating otitis which comprises introducing an anti-bacterially effective amount of a composition as described above topically to the site of infection or inflammation. A preferred method is instilling the composition into the ear. If the ear drum is perforated, the composition can penetrate to the middle ear. Otherwise the composition can be introduced into the middle ear, for example, through a myrogotomy tube, or through the Eustachian tube by the method described in German Patent No. DE 3,617,400. To some degree, the composition can also diffuse into adjoining tissues and the middle ear when an intact ear drum is present.

Effective amounts of composition for introduction into the ear are preferably one to five drops twice daily, that is, from about 40 to about 200 $\mu$l per application.

DESCRIPTION

According to this invention, water, being not ototoxic, irritating or sensitizing in the ear, is the base for a solution composition containing ciprofloxacin, which is highly antibacterial in otitis treatment. Amounts of ciprofloxacin in aqueous solution effective for anti-bacterial action range from about 0.01 to about 1 weight percent, preferably from about 0.1 to about 0.5 weight percent, most preferably about 0.2 weight percent.

To prevent contamination by microorganisms and provide a reasonable shelf life, the otic composition provided by this invention includes a preservative. The required properties for a preservative compatible with ciprofloxacin were met with difficulty. Acceptable preservatives were required to cause no or insignificant ototoxicity, sensitization or irritation of the ear. Another requirement was that the preservative be jointly soluble with ciprofloxacin in water over a common pH range inasmuch as ciprofloxacin solubility was limited to pH's less than about 6. In aqueous solutions containing from about 0.2 to about 1 weight percent of ciprofloxacin hydrochloride, crystalline precipitation was observed to occur at pH's above 5.5 at room temperature, and at pH's above 5 at 5 C.

Potassium sorbate, sodium benzoate and benzyl alcohol were candidate preservatives. In aqueous solutions at 5 C containing from about 0.2 to 0.3 weight percent sodium benzoate, precipitation of crystals was observed at pH's lower than about 4.5 to 5. In aqueous solutions at 5 C containing from about 0.1 to 0.15 weight percent potassium sorbate, precipitation of crystals was observed at pH's lower than 4.5. In view of the experimentally determined pH ranges for aqueous solubility of ciprofloxacin hydrochloride and potassium sorbate, aqueous solutions containing these materials preferably have a pH range of about 3 to about 6, most preferably, about 4.75.

Potassium sorbate in concentrations of 0.13, 0.104 and 0.065 weight percent; sodium benzoate in a concentration of 0.24 weight percent; and benzyl alcohol at concentrations of 0.9, 0.72 and 0.45 weight percent were found to be effective preservatives in aqueous ciprofloxacin hydrochloride solutions in preservative challenge tests conducted pursuant to the procedure described in the United States Pharmacopeia, Edition XXIII, 1995, page 1681, hereby incorporated by reference. Amounts of potassium sorbate effective as a preservative for ciprofloxacin hydrochloride in aqueous solution range from about 0.01 to about 1 weight percent, preferably from about 0.05 to about 0.5 weight percent, and most preferably about 0.13 weight percent. Amounts of benzyl alcohol effective as a preservative in aqueous preparations with ciprofloxacin hydrochloride range from about 0.1 to about 3 weight percent, preferably from about 0.1 to about 2 weight percent, and most preferably about 0.9 weight percent. The solubility of ciprofloxacin hydrochloride being unaffected by benzyl alcohol, solutions of these materials may have a pH below about 6, and preferably about 4.75.

Because the aqueous solubilities of ciprofloxacin hydrochloride and potassium sorbate are limited to a narrow mutual pH range, a buffering agent is desirable when potassium sorbate is used as a preservative in ciprofloxacin hydrochloride solutions. Citrate buffer caused precipitation of ciprofloxacin and was unsuitable. Acetate buffer was found effective at a concentration of 0.05 molar. Amounts of sodium acetate and acetic acid effective to buffer the preparation range from about 0.1 to about 3 weight percent of sodium acetate and from about 0.01 to about 10 weight percent of acetic acid; preferably from about 0.1 to about 2 weight percent of sodium acetate and from about 0.1 to about 5 weight percent of acetic acid; and most preferably about 0.4 weight percent of sodium acetate and about 0.7 weight percent of acetic acid.

Benzyl alcohol having a solubility in aqueous solutions independent of pH, and ciprofloxacin hydrochloride having solubility in aqueous solutions at pH less than about 6, solutions including these components do not need to be buffered, but may be simply adjusted with hydrochloric acid or sodium hydrochloride to a pH less than about 6, preferably to a pH of about 4.75. A buffer, however, such as an acetate buffer, may be included.

To allow the ciprofloxacin liquid preparation to be administered in drops from a medicine dropper, flow by gravity to, and remain or deposit in an effective amount at a desired area of topical application, a viscosity preferably greater than that of water was provided by including a viscosity augmenter. For compatibility with ciprofloxacin and other constituents of the preparation, preferred viscosity augmenters were non-ionic and unaffected by pH and ionic level. Aqueous solutions of ionic polymers such as carboxyvinyl polymer or polyacrylic acid, such as commercially available under the tradename Carbopol, and sodium carboxymethylcellulose were found to have undesirable viscosity variability with ionic level and pH. Other materials tried required undesirably high concentrations to produce a suitable level of viscosity. Example 1 below shows results for materials tested. All concentrations are in weight percent.

EXAMPLE 1

|  | Viscosity CTS |
| --- | --- |
| Hydroxypropylcellulose, 2% | 7.1 |
| Hydroxypropylmethylcellulose, | 13.7 |
| Cellulose gum, 0.5% | 16.3 |
| Carboxymethylcellulose, 1% | 11.2 |
| Polyvinyl alcohol, 4% | 24 |
| Polyvinylpyrrolidone, 20% | 16.7 |
| Polyvinylpyrrolidone, 30% | 63.7 |
| Methylcellulose, 0.5% | 13.3 |
| Methylcellulose, 0.65% | 49.4 |
| Carbopol, 0.02%, pH 4.7 | 18.5 |
| Carbopol, 0.036%, pH 3.9 | 4.7 |
| Carbopol, 0.036%, pH 4.75 | 203 |

Methylcellulose as commercially available under the tradename Methocel A4M from Dow Chemical Co. imparted an effective level of viscosity in low concentrations to the preparation. Amounts of methylcellulose effective to augment viscosity of aqueous solutions of ciprofloxacin hydrochloride range from about 0.1 to about 3 weight percent, preferably from about 0.1 to about 2 weight percent, and most preferably about 0.6 weight percent.

To allow the aqueous preparation to wet and spread on hydrophobic skin surface at the site of infection or inflammation in the ear canal, a surface active agent or surfactant was desirable. Non-ionic surfactants were indicated. The surfactant known as polysorbate, in particular ranging from polysorbate 20 to 80, commercially available under the tradename Tween from ICI Americas, Inc. in experimental determinations was found to provide satisfactory contact angle on hydrophobic surfaces of Teflon and clean glass. Polysorbate commercially available from other manufacturers, and in particular, conforming to USP or NF specifications is also suitable. Amounts of polysorbate ranging from polysorbate 20 to 80 effective for spreading the compositions of this invention on a hydrophobic skin surface range from about 0.01 to about 2 weight percent, preferably from about 0.05 to about 1 weight percent, and most preferably about 0.1 weight percent.

Approximate isotonicity was a desirable condition in the ciprofloxacin preparation, which was imparted by the addition of glycerin. Amounts of glycerin effective to adjust the tonicity of the composition to a level of from about 200 to about 600 milliosmoles range from about 0.1 to about 5 weight percent, preferably from about 0.1 to about 2 weight percent, and most preferably about 1 weight percent.

EXAMPLE 2

A batch of the solution composition provided by this invention was prepared by the following procedure. Glassware and passivated steel vessels and accessories free of visible iron ion residue such as rust were used exclusively. The preparation was conducted in the absence of daylight under sodium vapor lamps or yellow light. Transfers of solutions were made avoiding foaming. To 16364 grams of purified water heated to about 80 to 90 C was added with mixing 162.5 grams of methylcellulose, specifically, Methocel A4M, supplied by Dow Chemical Co. Mixing continued until the Methocel A4M was uniformly dispersed or dissolved. The solution was then cooled to about 20 to 25 C. To 500 grams of purified water was added 25 grams of Tween 20, USP/NF with mixing until dissolved. This Tween 20 solution was added to the Methocel A4M solution. Also added were 237.5 grams of glycerin, USP/NF and 63.75 grams of glacial acetic acid, USP/NF. Into 1510 grams of purified water was dissolved 170 grams of sodium acetate trihydrate, USP/NF and subsequently 335 grams of potassium sorbate, USP/NF. This solution was added to the Methocel A4M-Tween 20 solution. To the combined solutions was added 58.3 grams of ciprofloxacin hydrochloride as commercially available from Bayer AG of a purity corresponding to USP/NF. Sufficient water was added to bring the combined solution to 24500 ml, and then the pH was adjusted to a range of about 4.5 to about 5.0, preferably to about 4.75, with 1N hydrochloric acid or 1N sodium hydroxide. The total volume was brought up to 25000 ml with purified water and filtered. Portions of the solution were stored in 10 ml type 1 flint glass bottles at 50 C for three months without discoloration or other indication of instability. The composition of this batch is set out in Table 1 following.

TABLE 1

| Ingredient | Concentration Weight % |
| --- | --- |
| Ciprofloxacin hydrochloride | 0.2332 |
| Polysorbate 20 | 0.10 |
| Methylcellulose | 0.65 |
| Potassium sorbate | 0.134 |
| Sodium acetate | 0.41 |
| Acetic acid | 0.7 |
| Glycerin | 0.95 |
| Sodium hydroxide, 1N | as required |
| Hydrochloric acid, 1N | as required |
| Water | 96.8228 |

Other batches of solution with and without ciprofloxacin were prepared by the described procedure. Specimens of solutions with and without ciprofloxacin were shown to be non-ototoxic in guinea pig models.

EXAMPLE 3

Four groups, each consisting of a minimum of 5 male and 5 female NIH pigmented guinea pigs, received 10 μl of either: a solution of composition according to Table 1; a solution of composition according to Table 1 without ciprofloxacin; 0.9% sodium chloride; or 10% neomycin sulfate by direct application to the niche of the round window membrane via implanted cannula twice a day for 30 consecutive days. Hearing assessments were performed by auditory brain-stem response once pretreatment (baseline) and on days 14 and 30. Bodyweights were monitored on days 0, 14, and 30, and the animals were observed daily for clinical signs of systemic toxicity. At termination on day 30, the middle ear was examined grossly and the cochlea was removed for inner ear histologic evaluation. The hair cells in each cochlea were assessed using a photomicroscope under epiflourescent illumination, and counted to yield a cytocochleogram.

In each of the first three groups, a few animals exhibited a minor hearing loss (20–30 dB). However, these animals did not have an increased loss of inner ear cochlear hair cells. The hearing loss was considered to be of middle ear origin, associated with the fibrous tissue around the cannula implanted in the middle ear, and, thus not related to the administration of the test materials. In the fourth group, the 10% neomycin positive control caused a major functional hearing loss and a massive structural loss of inner and outer cochlear hair cells.

The other animals did not exhibit any appreciable hearing loss. The results of this study demonstrated that neither the solution of composition according to Table 1, with or without ciprofloxacin, nor saline, cause structural or functional ototoxicity. The dose volume used was approximately 50 times the volume anticipated to be present at the round window membrane in human treatment.

Another embodiment of the invention provides a non-ototoxic, non-irritating and non-sensitizing ciprofloxacin-containing otic composition suitable for the inclusion of the anti-inflammatory glucocorticoid agent hydrocortisone. Water, being not ototoxic, irritating or sensitizing in the ear, was employed as the composition base. Amounts of ciprofloxacin hydrochloride in aqueous solution effective for anti-bacterial action range from about 0.01 to about 1 weight percent, preferably from about 0.1 to about 0.5 weight percent, and most preferably about 0.2 weight percent. Amounts of hydrocortisone effective for anti-inflammatory action range from about 0.1 to about 3 weight percent, preferably from about 0.1 to about 2 weight percent, and most preferably about 1 weight percent.

The inclusion of hydrocortisone because of its very low solubility in water required development of an aqueous suspension of hydrocortisone with ciprofloxacin hydrochloride. A pharmaceutical composition desirably has a reasonable shelf life, preferably two years, for the convenience of the user. Thus any insoluble constituents should tend to remain in suspension, or be readily resuspended by moderate shaking of the container. Uniformity of dispersion and a high degree of dispersion throughout the composition in the container allow a uniform and repeatable dose to be withdrawn for delivery to the host.

Since redispersibility is one of the major considerations in assessing the acceptability of a suspension, and since the sediment formed should be easily dispersed by moderate shaking to yield a homogeneous system, measurement of the sedimentation volume and its ease of redispersion form two of the most common basic evaluative procedures according to the *Theory and Practice of Industrial Pharmacy* by L. Lochman, H. A. Lieberman, J. L. Kanig, 2nd Edition, pages 159, 180. The methods suggested in this text were adapted to assess resuspendability and sedimentation rate of candidate compositions and to discover materials enhancing the suspension of hydrocortisone in an aqueous base. Resuspendability of candidate constituents and compositions was assessed by the number of inversions, termed strokes, required to redisperse sedimentation which was visible in a bottle containing specimens of composition after standing undisturbed overnight. Sedimentation rate was assessed by observing the height in millimeters of the column of sedimentation visible in 20 milliliters of specimen suspension contained in a cylinder after shaking and then standing undisturbed overnight. Larger heights were favorable indicating less separation with less supernatant liquid and less compaction of sedimentation.

To allow a ciprofloxacin preparation to be administered in drops from a medicine dropper, flow by gravity to and remain or deposit in an effective amount at a selected area for topical application, a viscosity augmenting agent which would also serve to suspend hydrocortisone was desirable. A large number of agents were evaluated by the above procedure for their ability to suspend hydrocortisone in an aqueous solution of ciprofloxacin hydrochloride and augment viscosity of the composition to a viscosity greater than that of water. For compatibility with ciprofloxacin hydrochloride solubility, such agents were preferably non-ionic and unaffected by pH and ionic level. Aqueous solutions of ionic polymers such as Carbopol and sodiumcarboxymethylcellulose were found to have undesirable viscosity variability with ionic level and pH. Other materials tried required undesirably high concentrations to produce a suitable level of viscosity. Methylcellulose imparted an effective level of viscosity in low concentrations to the preparation, but was found ineffective in suspending hydrocortisone.

Polyvinyl alcohol in concentrations of about 2 weight percent produced a suitable viscosity and displayed a high ability to suspend hydrocortisone in aqueous preparations in tests performed as described above and shown in the following example employing 99% hydrolyzed polyvinyl alcohol.

EXAMPLE 4

| | |
|---|---|
| Strokes to redisperse after standing overnight | 4 |
| Specimen ht, original, mm | 50 |
| Sedimentation ht after standing overnight, mm | 9 |

In comparisons with compositions with fully dissolved polyvinyl alcohol, compositions with partially dissolved polyvinyl alcohol showed fewer strokes and larger sedimentation volume. However, because of anticipated variability and change in the amount dissolved over varying temperature conditions expected to occur in storage, compositions with fully dissolved polyvinyl alcohol were preferred. Polyvinyl alcohol in an 85% hydrolyzed grade was effective in suspending hydrocortisone. However, polyvinyl alcohol in a medium viscosity grade, 99% hydrolyzed, was determined to be superior in suspending hydrocortisone. Such material is commercially available under the tradename Airvol 125 from Air Products and Chemicals Inc. Amounts of polyvinyl alcohol effective to augment the viscosity of and to suspend hydrocortisone in aqueous compositions with ciprofloxacin hydrochloride range from about 0.1 to about 10 weight percent, preferably from about 1 to about 5 weight percent, and most preferably about 2 weight percent.

The addition of lecithin in a concentration of about 0.15 weight percent enhanced the efficacy of polyvinyl alcohol in suspending hydrocortisone in aqueous preparations with ciprofloxacin hydrochloride and other components. Two grades were evaluated in suspendability trials A fully hydrogenated soy lecithin comprising 90% phosphatidylcholine commercially available under the tradename Phospholipon 90H from American Lecithin Co. was efficacious. A soy lecithin comprising 75% phosphatidylcholine commercially available under the tradename Lipoid-S75 from Vernon Walden, Inc. also was efficacious. Amounts of lecithin effective to augment the suspension of hydrocortisone in aqueous compositions with ciprofloxacin hydrochloride and polyvinyl alcohol range from about 0.01 to about 5 weight percent, preferably from about 0.01 to about 2 weight percent, and most preferably about 0.15 weight percent.

To prevent contamination by microorganisms and provide a reasonable shelf life, inclusion of a preservative in the otic pharmaceutical preparation was desirable. The required properties for a preservative compatible with ciprofloxacin were met with difficulty. Acceptable preservatives were required to cause no or little ototoxicity, sensitization or irritation of the ear canal or middle ear. Another requirement was that the preservative be jointly soluble with ciprofloxacin in water over a common pH range inasmuch as ciprofloxacin solubility was determined to be limited to a narrow pH range. In aqueous solutions containing from about 0.2 to about 1 weight percent of ciprofloxacin hydrochloride, crystalline precipitation was observed to occur at pH's above 5.5 at room temperature, and at pH's above 5 at 5 C.

In suspendabilty trials, benzyl alcohol at concentrations of about 0.9 weight percent enhanced or did not impair the suspendability of hydrocortisone in the preparation. In preservative challenge tests conducted pursuant to the procedure described in the United States Pharmacopeia, Edition XXIII, 1995, page 1681, hereby incorporated by reference, benzyl alcohol was determined to be effective as a preservative at concentrations of 0.9, 0.72 and 0.45 weight percent in aqueous ciprofloxacin hydrochloride preparations. Amounts of benzyl alcohol effective as a preservative in aqueous preparations with ciprofloxacin hydrochloride range from about 0.1 to about 3 weight percent, preferably from about 0.1 to about 2 weight percent, and most preferably about 0.9 weight percent. The solubility of ciprofloxacin hydrochloride being unaffected by benzyl alcohol, solutions of these materials may have a pH below about 6, and preferably about 4.75.

Inclusion of a buffering agent, although not necessary, was preferred. Acetate buffer was found effective at a concentration of 0.05 molar. The acetate buffer was also determined to enhance or not impair the suspendability of hydrocortisone in the preparation. Amounts of sodium acetate and acetic acid effective to buffer the preparation range from about 0.1 to about 3 weight percent of sodium acetate and from about 0.01 to about 10 weight percent of acetic acid; preferably from about 0.1 to about 2 weight percent of sodium acetate and from about 0.1 to about 5 weight percent of acetic acid; and most preferably about 0.4 weight percent of sodium acetate and about 0.7 weight percent of acetic acid.

To allow the aqueous preparation to wet and spread on hydrophobic skin surface at the site of infection or inflammation in the ear canal, a surface active agent or surfactant was desirable. Non-ionic surfactants were indicated. The surfactant known as polysorbate, in particular ranging from polysorbate 20 to 80, commercially available under the tradename Tween from ICI Americas, Inc. in experimental determinations was found to provide satisfactory contact angle on hydrophobic surfaces of Teflon and clean glass. Polysorbate commercially available from other manufacturers, and in particular, conforming to USP or NF specifications is also suitable. Tween 20 and Tween 80, in concentration of 0.1 weight percent, were determined to be effective in enhancing or not impairing the suspendability of hydrocortisone in an aqueous preparation with ciprofloxacin hydrochloride and polyvinyl alcohol. Amounts of polysorbate ranging from polysorbate 20 to 80 effective for spreading the compositions of this invention on a hydrophobic skin surface range from about 0.01 to about 2 weight percent, preferably from about 0.05 to about 1 weight percent, and most preferably about 1 weight percent.

Approximate isotonicity was a desirable condition in the ciprofloxacin preparation, which was imparted by the addition of sodium chloride. Sodium chloride in concentrations of about 0.9 weight percent were determined to be effective in enhancing or not impairing the suspendability of hydrocortisone in an aqueous preparation with ciprofloxacin and other constituents. Amounts of sodium chloride effective to adjust the tonicity of the composition from about 200 to about 600 milliosmoles range from about 0.1 to about 5 weight percent, preferably from about 0.1 to about 2 weight percent, and most preferably about 0.9 weight percent.

EXAMPLE 5

A batch of the composition provided by this invention was prepared by the following procedure. Glassware and passivated steel vessels and accessories free of visible iron ion residue such as rust were used exclusively. The preparation was conducted in the absence of daylight under sodium vapor lamps or yellow light. Transfers of solutions were made avoiding foaming. Purified water in an amount of 15255 grams was heated to 90 to 95 C and then cooled to 20 to 25 C under a nitrogen environment, and held for later use for pre-mixing, rinsing, and final volume makeup. To 15255 grams of purified water heated to about 90 to 95 C was added with mixing until fully dissolved, 500 grams of polyvinyl alcohol. To this solution was added 36.5 grams of Phospholipon 90H (lecithin) with mixing until fully dispersed. While purging nitrogen into the headspace of the container of this solution, cooling to 40 to 50 C was started. To this solution was added 25 grams of benzyl alcohol, USP/NF with mixing until dissolved. Nitrogen purging and cooling was continued to 20 to 25 C. Mixed in was 63.75 grams of glacial acetic acid, USP/NF. In a separate container, 225 grams of sodium chloride, USP/NF and 170 grams of sodium acetate trihydrate, USP/NF were dissolved in 1525 grams of purified water and then added to the main batch. Into 2743 grams of purified water in a separate container, 25 grams of polysorbate 20, USP/NF was dissolved. Added was 250 grams of hydrocortisone, micronized, USP/NF with mixing until wetted and dispersed. Added and dissolved into the main batch under nitrogen purging, was 58.3 grams of ciprofloxacin hydrochloride, of a purity corresponding to USP/NF, equivalent to 0.2 weight percent ciprofloxacin. (Alternately, ciprofloxacin hydrochloride may be predisolved in approximately 3000 grams of water along with the glacial acetic acid and sodium acetate trihydrate, and then added to the main batch.) The hydrocortisone premix was added to the main batch and mixed. Purified water was added to bring the batch to 24500 milliliters, and the pH was adjusted to 4.75 using IN hydrochloric acid or IN sodium hydroxide. Purified water was added to bring the batch to 25000 milliliters. The composition of this batch is set out in Table 2 following.

TABLE 2

| Ingredient | Concentration Weight % |
|---|---|
| Ciprofloxacin hydrochloride | 0.2332 |
| Hydrocortisone | 1. |
| Polysorbate 20 | 0.10 |
| Polyvinyl alcohol | 2. |
| Phospholipon 90 H | 0.15 |
| Benzyl alcohol | 0.9 |
| Acetic acid | 0.7 |
| Sodium acetate | 0.41 |
| Sodium chloride | 0.9 |
| Sodium hydroxide, 1N | as required |
| Hydrochloric acid, 1N | as required |
| Water | 98.6068 |

Results of the dispersibility and settling test on a specimen of the composition set out above conducted pursuant to the procedure described above gave the results shown in the example below.

EXAMPLE 6

| | |
|---|---|
| Strokes to redisperse after standing overnight | 3 |
| Specimen ht, original, mm | 50 |
| Sedimentation ht after standing overnight, mm | 11 |

Specimens of this batch were stored at 5 C and at 50 C for one month. Other specimens were subjected to one week of freezing and thawing cycling. No appreciable change in either the sedimentation volume or redispersibility was noted in any of these. Results of a dispersibility and settling test on a specimen of the composition set out above after storage for one month at 50 C, conducted pursuant to the procedure described above gave the results shown in example below.

EXAMPLE 7

| | |
|---|---|
| Strokes to redisperse after standing overnight | 3–4 |
| Specimen ht, original, mm | 50 |
| Sedimentation ht after standing overnight, mm | 9–10 |

Other batches of the composition of Table 2, with and without ciprofloxacin, were prepared by the described procedure. Specimens of such preparations with and without ciprofloxacin were shown to be non-ototoxic in guinea pig animal models.

EXAMPLE 8

Three groups, each consisting of a minimum of 5 male and 5 female NIH pigmented guinea pigs, received 10 $\mu$l of either a composition according to Table 2; a composition according to Table 2 without ciprofloxacin; or a composition according to Table 2 without ciprofloxacin and hydrocortisone, by direct application to the niche of the round window membrane via implanted cannula twice a day for 30 consecutive days. Hearing assessments were performed by auditory brain-stem response once pretreatment (baseline) and on days 14 and 30. Body weights were monitored on days 0, 4, and 30, and the animals were observed daily for clinical signs of systemic toxicity. At termination on day 30, the middle ear was examined grossly and the cochlea was removed for inner ear histologic evaluation. The hair cells in each cochlea were assessed using a photomicroscope under epifluorescent illumination, and counted to yield a cytocochleogram.

One animal in the first group and one animal in the second group exhibited a minor hearing loss (20–40 dB). However, these animals did not have an increased loss of inner ear cochlear hair cells. The hearing loss was considered to be of middle ear origin, associated with the fibrous tissue around the cannula implanted in the middle ear, and thus, not related to the administration of the test materials.

The other animals did not exhibit any appreciable hearing loss. The results of this study demonstrated that none of the compositions applied cause either structural or functional ototoxicity.

Yet another embodiment of the invention provides a non-ototoxic, non-irritating and non-sensitizing ciprofloxacin-containing otic solution composition wherein glycerine augments the viscosity of the aqueous solution to a viscosity greater than that of water. Glycerine concentrations of from about So to about 95 weight percent provide usable viscosities ranging from about 10 to about 200 centistokes. Preferred glycerine concentrations range from about 70 to 90 weight percent, most preferably 87 weight percent. Concentrations of ciprofloxacin in such aqueous solutions effective for anti-bacterial action range from about 0.01 to about 1 weight percent, preferably from about 0.1 to about 0.5 weight percent, most preferably about 0.2 weight percent.

A buffer may be included to provide a pH range to maintain the solubility of ciprofloxacin hydrochloride in the composition. A range of pH of from about 3 to about 6 is suitable. Amounts of sodium acetate and acetic acid effective to buffer the composition range from about 0.01 to about 2 weight percent of sodium acetate and from about 0.01 to about 5 weight percent of acetic acid; preferably from about 0.02 to about 1 weight percent of sodium acetate and from about 0.1 to about 2 weight percent of acetic acid; and most preferably about 0.05 weight percent of sodium acetate and about 0.16 weight percent of acetic acid.

EXAMPLE 9

In accordance with this embodiment, a solution was prepared having 0.2 weight percent ciprofloxacin, 87.0 weight percent glycerine, 0.05 weight percent sodium acetate, 0.16 weight percent acetic acid, the balance being water. This composition was determined to be adequately resistant to contamination by microorganisms over a reasonable shelf life. However, a preservative, such as, for instance, potassium sorbate or benzyl alcohol, may be included for added protection. In view of the tests performed on guinea pigs with other compositions including the ingredients of this solution, this solution is non-ototoxic, non-sensitizing and non-irritating applied topically to the external and middle ear in humans.

The foregoing embodiments and examples are to be considered illustrative, rather than restrictive of the invention, and those modifications which come within the meaning and range of equivalence of the claims are to be included therein.

What is claimed is:

1. An aqueous non-ototoxic, topical, otic pharmaceutical composition of matter for treating a mammal consisting essentially of:

(a) ciprofloxacin or a pharmaceutically acceptable salt thereof in aqueous solution in an amount effective for antibacterial action;

(b) hydrocortisone or a pharmaceutically acceptable salt thereof in an amount effective as an anti-inflammatory agent,
(c) polyvinyl alcohol at least about 85% hydrolyzed in an amount effective to suspend the hydrocortisone in solution;
(d) water sufficient to produce an aqueous composition;
(e) benzyl alcohol in an amount effective for antibacterial action;
(f) lecithin in an amount effective for enhancing suspension of other constituents in the composition; and
(g) polysorbate ranging from 20polysorbate 20 to 80 in an amount effective for spreading the preparation on a hydrophobic skin surface to the site of infection or inflammation.

2. The composition of claim 1 further comprising ciprofloxacin present from about 0.01 to 1.0 weight percent.

3. The composition of claim 1 further comprising hydrocortisone present from about 0.1 to 3.0 weight percent.

4. The composition of claim 1 further comprising polyvinyl alcohol present from about 0.1 to 10.0 weight percent.

5. The composition of claim 1 further comprising lecithin from about 0.01 to 5.0 weight percent.

6. The composition of claim 1 further comprising benzyl alcohol present from about 0.1 to 3 weight percent.

7. The composition of claim 1 further comprising acetate buffer at about 0.05 molar.

8. The composition of claim 1 further comprising polysorbate from about 0.01 to 2 weight percent.

9. The composition of claim 1 further comprising sodium chloride from about 0.1 to 5 weight percent.

10. The composition of claim 1 further comprising polyvinyl alcohol at least about 99% hydrolyzed.

* * * * *